US008759608B2

(12) United States Patent
Chen et al.

(10) Patent No.: US 8,759,608 B2
(45) Date of Patent: Jun. 24, 2014

(54) METHOD OF CREATING A SPRING BRASSICA NAPUS

(75) Inventors: Zhizheng Chen, Fort Collins, MN (US); Benyuan Dang, Fort Collins, MN (US); Daren Kenneth Coonrod, Fort Collins, MN (US)

(73) Assignee: Cargill, Incorporated, Wayzata, MN (US)

( * ) Notice: Subject to any disclaimer, the term of this patent is extended or adjusted under 35 U.S.C. 154(b) by 61 days.

(21) Appl. No.: 13/375,358

(22) PCT Filed: Jun. 1, 2010

(86) PCT No.: PCT/US2010/036911
§ 371 (c)(1),
(2), (4) Date: Nov. 30, 2011

(87) PCT Pub. No.: WO2010/141476
PCT Pub. Date: Dec. 9, 2010

(65) Prior Publication Data
US 2012/0073009 A1 Mar. 22, 2012

Related U.S. Application Data

(60) Provisional application No. 61/217,513, filed on May 31, 2009.

(51) Int. Cl.
*A01H 5/10* (2006.01)
*A01H 1/04* (2006.01)
*A01H 5/00* (2006.01)

(52) U.S. Cl.
USPC .......................................... 800/269; 800/306

(58) Field of Classification Search
None
See application file for complete search history.

(56) References Cited

U.S. PATENT DOCUMENTS

| | | | |
|---|---|---|---|
| 5,107,064 A | 4/1992 | Williams et al. | |
| 6,069,302 A | 5/2000 | Osborn et al. | |
| 6,140,085 A | 10/2000 | Dean et al. | |

OTHER PUBLICATIONS

Van Deynze et al., Euphytica, (1994), 74: pp. 77-83.*
Qian et al., Theor. Appl. Genet, (2006), 113: pp. 49-54.*
Allard, "Principles of Plant Breeding", New York: John wiley & Sons, Inc. 1960, 485 pages, p. 154-157.
Deng et al. "Involvement of the Histone Acetyltransferase AtHAC1 in the Regulation of Flowering Time via Repression of Flowering Locus C in *Arabidopsis*," Plant Physiology, Ap, Apr. 2007.
Howell et al., "A and C Genome Distinction and Chromosome Identification in *Brassica napus* by Sequintial Fluorescence in Situ Hybridization and Genomic in Situ Hybridization", Dec. 2008.
Iniguez-Luy et al., "Development of public immortal mapping populations, molecular markers and linkage maps for rapid cycling *Brassica rapa* and *B. oleracea*" Springer-Verlag 20, Sep. 2009.
Murphy et al., "Inheritance of the Vernalization Response Determined by Doubled Haploids in Spring Oilseed Rape (*Brassica napus* L.)," Crop Sci. 98: p. 1463-1467; 1998.
Rife et al., "Cold Tolerance in Oilseed Rape over Varying Acclimation Durations," Crop Sci: 43: p. 96-100; 2003 1.
Quijada et al., "Phenotypic Effects of Introgressing French Winter Germplasm into Hybrid Spring Canola," Crop Sci. 44: p. 1982-1989; 2004.
Williams et al,, "Rapid-Cycling Populations of *Brassica*," Science, vol. 232, p. 1385-1389; Jun. 13, 1986.
Wisconsin Fast Plants Program, "Introduction to Fast Plants," University of Wisconsin Madison; www.fastplants.org/intro.php, Apr. 20, 2009.
Wisconsin Fast Plants Program, "The Story of the First Fast Plants," University of Wisconsin Madison; www.fastplants.org/intro.story.php, Apr. 20, 2009.
Zanewich et al., "Vernalization and Gibberellin Physiology of Winter Canola," Plant Physiol.; 1995; vol. 108; p. 615-621.
AgBiotech Bulletin, "Lighting the Way," vol. 8, Issue 11, Dec. 2000; Published by AG-West Biotech Inc.

* cited by examiner

*Primary Examiner* — David T Fox
*Assistant Examiner* — Jared Shapiro

(57) ABSTRACT

Crossing a winter *B. napus* line with a rapid-cycle *B. rapa* line has been discovered to provide an unexpectedly simple and efficient way to create a modified *B. napus* with a spring flowering habit. In one implementation, such a modified *B. napus* or its progeny is crossed with a second winter *B. napus* line to produce a plant having a winter flowering habit. This allows one to significantly shorten the development cycle for winter-flowering *B. napus* lines by conducting part of the breeding program with spring-flowering time cycles, then migrating the resultant germplasm back into a winter-flowering line.

19 Claims, No Drawings

METHOD OF CREATING A SPRING *BRASSICA NAPUS*

CROSS-REFERENCE TO RELATED APPLICATIONS

This is a national phase entry of International Application No. PCT/US2010/036911, filed 1 Jun. 2010 and entitled METHOD OF CREATING A SPRING BRASSICA NAPUS, which claims the benefit of U.S. Provisional Application No. 61/217,513, filed 31 May 2009 and entitled METHOD OF CREATING A SPRING BRASSICA NAPUS.

TECHNICAL FIELD

The present disclosure relates generally to breeding of *Brassica napus*. The invention has particular utility in creating spring *B. napus* lines from winter *B. napus* lines.

BACKGROUND

*Brassica napus* is grown commercially to produce edible oil that is low in saturated fat. In Europe, *B. napus* is commonly referred to as rapeseed or rape. Most *B. napus* commercially produced in North America is canola, which by definition must produce seed that yields oil having less than 2% erucic acid and meal that contains no more than 30 micromoles of the following glucosinolates per gram of air-dry, oil-free solid: 3-butenyl glucosinolate, 4-pentenyl glucosinolate, 2-hydroxy-3 butenyl glucosinolate, and 2-hydroxy-4-pentenyl glucosinolate. As used herein, a "non-canola" *B. napus* line is one which does not meet this definition, e.g., because the seeds produce oil with too much erucic acid or have too high a glucosinolate level.

Most *B. napus* lines are typically classified as either spring lines or winter lines. Winter lines are commonly planted in the autumn and flower in the spring after a period of vernalization over the winter. Spring lines do not require vernalization to flower and are commonly planted and harvested in the same growing season. Winter lines are common in Europe, but most winter lines fare poorly in the colder winters of Canada and the northern United States. As a consequence, most *B. napus* grown commercially in North America are spring lines.

Although open-pollinated *B. napus* lines remain quite common, commercial production of spring *B. napus* increasingly employs hybrid lines. Hybrid lines tend to have higher yields due to heterosis or "hybrid vigor". This heterosis is more pronounced the more distant the genetic relationship between the parent *B. napus* lines.

For this reason, several researchers have suggested crossing winter and spring *B. napus* lines to produce higher-yielding hybrids. For example, U.S. Pat. No. 6,069,302 ("Osborn", the entirety of which is incorporated herein by reference) proposes crossing a spring *B. napus* line with a *B. napus* line that is itself derived from at least one winter line.

DETAILED DESCRIPTION

Definitions

As used herein, a "winter *B. napus*" is a *B. napus* that has a winter flowering habit, i.e., that does not germinate, initiate vegetative growth, undergo gametogenesis and flower in less than 77 days when subjected to the following conditions, which are referred to below as "standardized growing conditions" or simply "SGCs": the seeds are planted in 4-inch plastic pots in a general growth medium (e.g., Premier Pro-Mix BX potting soil from Permier Horticulture of Quebec, Canada) in an environmentally controlled growth cabinet (e.g., Conviron ATC60 from Controlled Environments Limited of Winnipeg, Manitoba) with a 16 hour photoperiod, a day time temperature of 20 degrees Celsius and night time temperature of 17 degrees Celsius, watered daily as needed and a 20:20:20 (NPK) liquid fertilizer added three times weekly.

As used herein, a "spring *B. napus*" is a *B. napus* that has a spring flowering habit, i.e., that will germinate, initiate vegetative growth, undergo gametogenesis and flower in no more than 55 days when subjected to the aforementioned standardized growing conditions.

A "rapid-cycle *Brassica rapa*", as that term is used herein, is a *B. rapa* that has a rapid-cycle flowering habit, i.e., that will germinate, initiate vegetative growth, undergo gametogenesis and flower in no more than 20 days when subjected to the standardized growing conditions detailed above. As it flowers in less than 55 days, a "rapid-cycle *Brassica rapa*" may also be said to have a spring flowering habit.

Overview

Specific details of several embodiments of the disclosure are described below. One aspect of the present disclosure is directed toward a method for producing a modified *Brassica napus*. In accordance with this method, a first winter *B. napus* line is crossed with a rapid-cycle *B. rapa* line in a first cross, thereby producing an F1 modified *B. napus* plant that has a spring flowering habit. The rapid-cycle *B. rapa* line has a mean flowering time under standardized growing conditions of no greater than 20 days. After the first cross, seed from the F1 modified *B. napus* plant (or progeny thereof) is crossed with a second winter *B. napus* line in a second cross to produce a plant, which may be referred to as a first backcross (BC1) plant, that has a spring flowering habit.

Another embodiment of the invention provides a method for producing a modified *Brassica napus* having a winter flowering habit. In this method, a first winter *B. napus* line is crossed with a rapid-cycle *B. rapa* line in a first cross, thereby producing an F1 modified *B. napus* plant that has a spring flowering habit. The rapid-cycle *B. rapa* line has a mean flowering time under standardized growing conditions of no greater than 20 days. After the first cross, the F1 modified *B. napus* plant (or progeny thereof) is crossed with a second winter *B. napus* line in a second cross to produce a first backcross population. From the first backcross population, at least one first backcross (BC1) plant that has a spring flowering habit is selected. Thereafter, the BC1 plant or progeny thereof is crossed with a third winter *B. napus* line in a third cross to produce a second backcross plant population. From the second backcross plant population, at least one second backcross (BC-W) plant that has a winter flowering habit is selected.

Producing F1 Spring *B. napus*

Aspects of the invention are directed to the production of a spring modified *B. napus* line by crossing a winter *B. napus* line with a rapid-cycle *Brassica rapa* line. In a preferred embodiment, the winter *B. napus* line used in the cross will not germinate, initiate vegetative growth, undergo gametogenesis and flower at all unless subjected to vernalization. Although this is no guarantee, a line that is less prone to flower without vernalization may have a more distant genetic relationship to most common spring *B. napus* lines (defined below). As a consequence, one might predict that crossing such a winter *B. napus* line with a common spring *B. napus* line would yield a hybrid with greater heterosis than would a winter line that flowers more readily.

Several restriction fragmentation length polymorphisms (RFLPs) have been linked to specific vernalization-responsive flowering time loci. See, e.g., Ferreira, M. E., et al., "Mapping Loci Controlling Vernalization Requirement and Flowering Time in *Brassica napus*," *Theor. Appl. Genet.* 98:727-732 (1995); see also Osborn, T. C. et al, "Comparison of Flowering Time Genes in *Brassica rapa, B. napus*, and *Arabadopsis thaliana*," *Genetics* 146:1123-1129 (1997). These include vfn1, which was mapped as a quantitative trait locus (QTL) of Linkage Group (LG) 9; vfn2, which was mapped as a QTL of LG12; and vfn3, which was mapped to LG16. Osborn identifies suitable RFLP loci to distinguish winter and spring vfn1 and vfn2 alleles and provides sequences that may be used for PCR probes to screen for winter vfn1 and vfn2 alleles.

Winter *B. napus* lines suitable for use in the present method may (but need not) have winter alleles for one, two, or three of the vfn1, vfn2, and vfn3 loci. In one useful implementation, the winter *B. napus* line used in the present method has a homozygotic winter vfn1 allele.

A wide variety of suitable winter *B. napus* lines are known and available to breeders from a variety of sources. A non-limiting, partial list of winter *B. napus* lines that are expected to work well in connection with the disclosed process would include Columbus, Jetton, Darmor, Campala, Casino, Bristol, Plainsman, Jet Neuf, Wichita, Major, Samourai, and Ceres. Some of these winter lines are European *B. napus* lines while others are North American winter lines. As explained below, spring modified *B. napus* lines of the present disclosure may be useful in creating hybrid spring *B. napus* lines. If such hybrid *B. napus* lines employ a parent line derived primarily from North American sources, using European winter *B. napus* lines in the present method may provide a rich source for diverse genetics that may further enhance heterosis.

In one embodiment, the winter *B. napus* line is a canola-quality line, i.e., it produces seed with oil having no more than 2% erucic acid and meal that contains no more than 30 micromoles of the previously identified glucosinolates per gram of meal. This can help quickly produce a canola-quality modified *B. napus* in accordance with the invention. In another useful approach, however, the winter *B. napus* line is not a canola line, e.g., because the glucosinolate level in its meal is too high. Many European varieties of *B. napus* do not meet the definition of canola. As explained below, using such varieties in this first cross can improve heterosis in further hybrid breeding.

Suitable rapid-cycle *B. rapa* lines are available under the trade name Wisconsin Fast Plants and available from multiple sources, including Carolina Biological Supply Company of Burlington, N.C., US ("Carolina"). The Fast Plant Standard seed from Carolina is expected to work well, though the other seed types offered by Carolina may be useful for specific breeding goals.

In one implementation, this cross employs a female winter *B. napus* line and a male rapid-cycle *B. rapa* line. The female line may exhibit cytoplasmic male sterility or may be emasculated manually. The pollen from the *B. rapa* line would then be available to pollinate the *B. napus* line. In other embodiments, the *B. rapa* may be the female line (e.g., by manual emasculation) and the *B. napus* may be the male line.

As noted above, the present disclosure provides a method in which a winter *B. napus* line is crossed with a rapid-cycle *B. rapa* line to produce at least one F1 plant that is a modified *B. napus* line. *B. napus* is commonly understood to be an allopolyploid with an "A" genome traceable to *B. rapa* and a "C" genome traceable to *Brassica oleracea*. Crossing *B. napus* and *B. rapa* in accordance with embodiments of the present invention, therefore, is believed to modify the A genome of the winter *B. napus* line while leaving the C genome largely intact. Those skilled in the field may refer to the F1 plant as a *B. napus* or as a "modified" *B. napus*, with "modified" possibly being further characterized as a "partially reconstituted" or "species interspecific". For purposes of clarity, the term "modified *B. napus*" shall be deemed to encompass plants that result from a cross of a *B. napus* line and a *B. rapa* line, as well as progeny of such a cross. Furthermore, the term *B. napus* as used herein shall encompass both conventional and modified *B. napus*.

A surprisingly high percentage of the F1 plants that come from the described *B. napus*×*B. rapa* cross are spring *B. napus*. It is worth noting that the scope of a spring flowering habit encompasses a rapid-cycle flowering habit, as well. Spring F1 plants of the present invention could, but certainly need not, have a rapid-cycle flowering habit.

Many commercially desirable F1 plants will have a spring flowering habit, but not a rapid-cycle flowering habit, i.e., will germinate, initiate vegetative growth, undergo gametogenesis and flower in 21-55 days under SGCs. Although rapid flowering is a desirable characteristic, rapid-cycle *B. rapa* may have a rather short time from planting to full maturity. The Wisconsin Fast Plant Program indicates that the Wisconsin Fast Plants, for example, mature within about 40 days after planting. Shorter growing seasons for *B. napus* are typically associated with reduced yield and/or lower oil quality, so a very short time to maturity may be expected to adversely impact yield and/or oil quality. Aspects of the present invention, however, yield spring *B. napus* lines that are expected to have very good agronomic and oil quality characteristics.

The resultant F1 hybrid may or may not produce canola-quality seed. If a non-canola *B. napus* is used as the winter line in making the F1, there is a good chance that some or all of the resultant F1 plants will produce seed that fail to meet the canola definition stated above. In one implementation, the F1 plants may be screened to identify seed that both has a spring flowering habit and produces canola-quality seed.

As noted above, Osborn and others have proposed crossing winter and spring *B. napus* lines and selecting spring *B. napus* plants from the resultant F1 population. Unfortunately, many of the plants in the F1 population are not spring *B. napus*. Osborn suggests using genetic screening of vfn1, vfn2, and/or vfn3 loci to identify plants that are expected to have a spring growth habit (as that term is used in the Osborn patent). Such screening may be less expensive than growing all of the F1 population to see which plants will have a spring flowering habit, but it adds complexity to a breeding program.

Aspects of the present invention provide a surprisingly high spring conversion efficiency, where "spring conversion efficiency" is the percentage of the F1 population resulting from the winter *B. napus*×rapid-cycle *B. rapa* cross that has a spring flowering habit. In certain implementations, this spring conversion efficiency is at least 80%, desirably 85% or more, and preferably at least 90%. As explained in connection with the examples below, winter *B. napus*×rapid-cycle *B. rapa* crosses have yielded an astounding 100% spring conversion rate in this first cross, i.e., all of the F1 plants have a spring flowering habit.

Backcrossing Spring *B. napus* with Winter *B. napus*

In accordance with a further embodiment, the F1 seeds produced by the winter *B. napus*×rapid-cycle *B. rapa* cross outlined above (or progeny of the F1 seed) are crossed again with a second winter *B. napus* line to yield a first backcross plant (BC1). The F1 seed used in this second cross desirably has a spring flowering habit. At least a significant percentage, if not all or substantially all, of the BC1 plants may have a spring flowering habit.

In one embodiment, this second cross is a true backcross, i.e., the same winter *B. napus* used in the first cross is used in the second cross with the F1 seed. In other embodiments, the first winter *B. napus* line used in the first cross is different from the second winter *B. napus* line used in the second cross. This may not be considered a true "backcross" as that term is conventionally used, but the term backcross as used herein in connection with producing the present BC1 plant (and subsequent BCn plants) is intended to encompass a cross of a spring modified *B. napus* F1 (or BCn) plant as described above with any suitable winter *B. napus* line. Even if there is no recurrent parent in the cross pollination, the term "backcross" is intended to reflect the cross a spring modified *B. napus* or its progeny "back" with any winter line.

The resultant BC1 seed may be subjected to any number of additional "backcrosses" with winter *B. napus*. Preferably, the BC1 seed used in such an additional backcross has a spring flowering habit; if the BC1 population includes some plants that do not have a spring flowering habit, one can test the BC1 seed and select only those plants that have a spring flowering habit. In some embodiments, each of these backcrosses is a true backcross, i.e., the winter line is the same in the first cross to produce the F1 seed and in each of the subsequent crosses. In other embodiments, the winter line used in a subsequent cross may differ from one or more of the winter line(s) used in the previous crosses. For example, the BC1 seed may be crossed with a third winter *B. napus* line to produce a second backcross plant (BC2) and the third winter *B. napus* line may be different from one or both of the first and second *B. napus* lines used to produce the F1 and BC1 plants, respectively.

This process may be repeated to create a whole series of backcross generations, BC1, BC2, BC3, . . . BCn. In each backcross, the winter parent may be a recurring parent from the preceding cross (a true backcross). Alternatively, two or more different winter lines may be used in the backcrosses. In each such backcross, a backcross population may be created and plants having a spring flowering habit may be selected from that population.

Further Hybrid Breeding—Spring

In another further embodiment, seed produced by crossing the winter *B. napus* line and rapid-cycle *B. rapa* line as noted above can be crossed in a second hybrid cross with another spring *B. napus* to produced a second hybrid *B. napus*, referred to herein as a F'1 hybrid, with a spring flowering habit. In this embodiment, the F1, BC1, BC2, . . . BCn seed described above, or progeny of such seed, may be used in the second hybrid crossing step. If so desired, seed from a suitable F1 or BCn plant having a spring flowering habit may be selfed one or more times to increase the amount of available seed. The selected seed (whether a selected F1 or BCn plant or the higher volume of seed from selfing) may be crossed with an existing spring *B. napus* line to form F'1 plants and plants having a spring flowering habit may be selected from the F'1 population.

Such an approach can be particularly advantageous in breeding a commercial canola line, for example. As noted above, the winter *B. napus* line selected for the initial cross to form the F1 hybrid may be a non-canola line. The genetic differences of such lines from most commercial spring canola lines will tend to be greater than such differences from most winter canola lines. At least some of this genetic difference is expected to be found in the F1 seed and in backcrosses and other progeny thereof. When the F1 seed is crossed with an existing spring *B. napus* line, the genetic differences between the two parent lines may enhance heterosis, producing F'1 plants that have better yield and/or vigor.

In one specific embodiment, therefore, the F1 line (or its progeny) selected for the second hybrid cross is a non-canola line. This non-canola F1 line is then crossed with a spring *B. napus* line that meets the canola definition and the resultant F'1 plants may be screened to select those that are canola quality.

As explained above, crossing *B. napus* and *B. rapa* in accordance with the present invention is believed to modify the A genome of the winter *B. napus* line while leaving the winter line's C genome largely intact. This means that a significant majority of the winter line's genetics will be carried forward into the modified *B. napus* F1 plants that result from *B. napus*×*B. rapa* cross.

In contrast, crossing spring×winter *B. napus* as proposed by Osborn results in modification of both the A and C genomes. Osborn teaches selecting a F1 plant from such a cross that has a spring growth habit and crossing that F1 plant with another spring line. This further dilutes the winter germplasm in the spring-stable line. Creating a spring modified *B. napus* and "backcrossing" that F1 plant (or its progeny) with another winter line, however, reinforces the winter genetics in the A genome while retaining a winter-derived C genome.

Methods in accordance with embodiments of the invention thus introduce significant new germplasm from winter lines' C genome into a spring *B. napus* breeding program. This largely untapped pool of germplasm is expected to increase heterosis in spring *B. napus* hybrids such as the F'1 plants noted above. As heterosis is associated with increased yield, this is expected to enable higher-yielding *B. napus* varieties.

Further Hybrid Breeding—Winter

Aspects of the invention can also be used to substantially speed up a winter *B. napus* breeding program. In accordance with one such method, a spring BC1 *B. napus* such as that described above is crossed with a winter line to form a backcross population. At least one second backcross plant that has a winter flowering habit is selected from that backcross population; this winter plant is referred to below as a BC-W to note its winter flowering habit. As a result, the breeding program takes a winter *B. napus*, creates a spring *B. napus* in which much of the winter C genome is believed to be intact, and then converts that spring *B. napus* back into a winter *B. napus*. Particularly if the first and second backcrosses are true backcrosses employing the same winter line used in the first cross with the rapid cycle *B. rapa*, this can leave some key genetics in the winter line intact through the complete cycle.

This embodiment process has particular commercial significance if multiple crosses are conducted using plants with a spring flowering habit before selecting the BC-W line with the winter flowering habit. As noted above, a series of backcross generations—BC1, BC2, . . . BCn—may be created. The spring conversion efficiency of these backcrosses remains fairly high even through multiple generations, so one can continue to select a plant from the backcross population that has a spring flowering habit.

Because most winter *B. napus* lines require vernalization, the time from planting to maturity for a winter *B. napus* is significantly longer than that for a spring *B. napus*. This means that spring breeding programs can take advantage of more greenhouse cycles per year than a similar winter breeding program, reducing the total time to develop a desired trait.

Employing the present embodiment, however, a winter breeder can achieve much the same greenhouse cycle times as a spring breeding program by using the BC1-BCn spring *B.*

*napus* generations described above. As each of these "backcrosses" permits the introduction of another winter *B. napus* line, the development time of the winter *B. napus* traits is greatly reduced. Once the breeder has developed such a spring *B. napus* with the desired traits, that spring *B. napus* can be crossed with another winter *B. napus* to create a backcross population and a resultant plant having a winter flowering habit may be selected from that population. This new winter *B. napus* line can then be used in the breeder's standard winter breeding program.

Because the rapid-cycle *B. rapa* appears to impact only the A genome in the F1 generation and the C genome from the winter parent(s) appears to be largely intact, a winter breeder can carry many of the traits of interest from his or her winter lines through multiple generations of spring breeding. When the breeder selects a plant with a winter flowering habit (referred to as BC-W above) from a backcross population, therefore, there appears to be a good likelihood of successfully carrying forward the developed trait from the spring backcross generations into the BC-W plant and its progeny.

EXAMPLES

Aspects of certain methods in accordance with embodiments of the invention are illustrated in the following examples.

Example 1

F1 Hybrid Cross

Seeds of three winter *B. napus* lines—Columbus, Jetton, and Darmor—were planted and stored in cold conditions for three months for vernalization before being moved to a greenhouse. Fast Plant Standard seed from Carolina, identified below as FPS, was found to flower in 18 days at SGCs so it was determined to have a rapid-cycle flowering habit. Another *B. rapa* line, AcBoreal, was found to flower at 27 days at SGCs, so it has a spring flowering habit and is not a rapid-cycle *B. rapa* line.

Each of the three winter *B. napus* lines were crossed with each of the *B. rapa* lines to make 5 plants of each cross. The winter *B. napus* lines were male sterile (they were emasculated or exhibited genetic cytoplasmic male sterility) and served as the female parent; the *B. rapa* lines were used as the male parent. The resultant F1 populations of each cross were grown under SGCs to determine their time to flowering. The time to the earliest flowering was noted for those plants that did flower; if no flowers were seen within 4 months at SGCs, the plant as noted as non-flowering. The results are shown in Table 1.

The spring conversion efficiency results for these crosses are remarkable. Crossing the winter *B. napus* lines with AcBoreal, a *B. rapa* with a spring flowering habit, produced an F1 population in which every single plant had a winter flowering habit, demonstrating a spring conversion efficiency of 0% (0 of 5 plants). Every F1 plant produced by crossing the rapid-cycle *B. rapa* FPS line with the same winter *B. napus* lines had a spring flowering habit, showing a remarkable 100% spring conversion efficiency (5 of 5 plants). This 100% spring conversion efficiency is impressive in its own right, but is made even more remarkable in comparison to the cross with AcBoreal, which itself has a spring flowering habit but did not yield a single F1 plant with a spring flowering habit.

Example 2

Backcross 1 (BC1)

Seed from one of the F1-C plants (Columbus×FPS cross) and one of the F1-J plants (Jetton×FPS cross) were then backcrossed to the original parent line, i.e., the F1-C was backcrossed with Columbus and the F1-J was crossed with Jetton. Twenty plants of each cross were produced. In each instance the winter *B. napus* line was used as the male and the F1 seed produced in Example 1 was used as the female. The resultant backcrossed seed (BC1) was planted and grown at SGCs and the time to the earliest flowering was noted for those plants that did flower; if no flowers were seen within 4 months at SGCs, the plant as noted as non-flowering. The results are shown in Table 2.

TABLE 2

| Female Parent (Winter *B. napus*) | Male Parent | Plant ID | Total Plants | Flowering Plants (%) | Days of Earliest Flower (SGCs) |
|---|---|---|---|---|---|
| Columbus | F1-C | BC1-C | 20 | 8 (40%) | ~30-43 |
| Jetton | F1-J | BC1-J | 20 | 1 (5%) | ~40 |

Example 3

Backcross 2 (BC2)

Seed from the plant with the shortest flowering time for each backcross in Example 2 was then used as the male line in a cross with a female winter line. The Jetton backcross (BC1-J) was backcrossed to Jetton and the Columbus backcross (BC1-C) was "backcrossed" with a variety of different winter lines, as noted in Table 3. Ten to twenty-five plants of each cross were produced, also as noted in Table 3. The resultant

TABLE 1

| Female Parent (winter *B. napus*) | Male Parent (*B. rapa*) | Plant ID | Total Plants | Flowering Plants (%) | Days of Earliest Flower (SGCs) | Flowering Habit |
|---|---|---|---|---|---|---|
| Columbus | FPS | F1-C | 5 | 5 (100%) | ~30-35 | Spring |
|  | AcBoreal |  | 5 | 0 | Non-flowering | Winter |
| Jetton | FPS | F1-J | 5 | 5 (100%) | ~35-40 | Spring |
|  | AcBoreal |  | 5 | 0 | Non-flowering | Winter |
| Darmor | FPS | F1-D | 5 | 5 (100%) | ~30-35 | Spring |
|  | AcBoreal |  | 5 | 0 | Non-flowering | Winter | backcrossed seed (BC1) was grown at SGCs and the time to the earliest flowering was noted for those plants that did flower; if no flowers were seen within 4 months at SGCs, the plant was noted as non-flowering.

TABLE 3

| Female Parent (Winter B. napus) | Male Parent | Plant ID | Total Plants | Flowering Plants (%) | Spring Plants (percentage of total plants) | Days of Earliest Flower (SGCs) |
|---|---|---|---|---|---|---|
| Columbus | BC1-C | BC2-C | 20 | 15 (75%) | 12 (60%) | 30 |
| Jetton | BC1-J | BC2-J | 25 | 20 (80%) | 18 (72%) | 31 |
| Campala | BC1-C | F1(BC2)-A | 20 | 18 (90%) | 17 (85%) | 32 |
| Casino | BC1-C | F1(BC2)-B | 20 | 18 (90%) | 13 (65%) | 34 |
| Bristol | BC1-C | F1(BC2)-C | 20 | 19 (95%) | 16 (80%) | 33 |
| Plainsman | BC1-C | F1(BC2)-D | 10 | 9 (90%) | 8 (80%) | 32 |
| Jet Neuf | BC1-C | F1(BC2)-E | 20 | 20 (100%) | 20 (100%) | 28 |
| Wichita | BC1-C | F1(BC2)-F | 20 | 20 (100%) | 20 (100%) | 27 |

The results of this experiment show that the spring conversion efficiency remains quite high even though the male parent is already a backcross. All of the backcrosses had a spring conversion efficiency of at least 60%, with the entire population resulting from two of the crosses having a spring flowering habit. This suggests that a substantial majority of the winter genetics can be retained in a BC2 generation seed that has a spring flowering habit.

Example 4

Backcross 3 (BC3)

Seed that flowered in Example 2 was used as the male parent in a cross with a winter line. In each case, a true backcross was made, e.g., BC2-C was crossed with Columbus. In addition, the earliest-flowering plant of the Wichita cross in Example 2 (designated F1(BC2)-F) was backcrossed with different winter varieties, as noted below in Table 4. Twenty plants of each such cross were grown at SGCs and the time to the earliest flowering was noted for those plants that did flower; if no flowers were seen within 4 months at SGCs, the plant as noted as non-flowering. For purposes of comparison, a known spring B. napus, Westar, was also planted under SGCs and the days to flower were noted.

TABLE 4

| Female parent (Winter B. napus) | Male Parent | Plant ID | Total Plants | Days of Earliest Flower (SGCs) |
|---|---|---|---|---|
| Columbus | BC2-C | BC3-C | 20 | 46 |
| Jetton | BC2-J | BC3-J | 20 | 50 |
| Campala | F1(BC2)-A | BC1(BC3)-A | 20 | ~80 |
| Casino | F1(BC2)-B | BC1(BC3)-B | 20 | 56 |
| Bristol | F1(BC2)-C | BC1(BC3)-C | 20 | 47 |
| Plainsman | F1(BC2)-D | BC1(BC3)-D | 20 | 52 |
| Jet Neuf | F1(BC2)-E | BC1(BC3)-E | 20 | 52 |
| Wichita | F1(BC2)-F | BC1(BC3)-F | 20 | 37 |
| Eric | F1(BC2)-F | F1(BC3)-G | 20 | 48 |
| Navajo | F1(BC2)-F | F1(BC3)-H | 20 | 48 |
| Contact | F1(BC2)-F | F1(BC3)-I | 20 | 55 |
| Mohican | F1(BC2)-F | F1(BC3)-J | 20 | 46 |
| Westar (spring) | — | — | 5 | 37 |

Ten of the twelve backcrosses produced in accordance with an embodiment of the invention had a spring flowering habit. Of the two exceptions—the Campala backcross, BC1(BC3)-A, and the Casino backcross, BC1(BC3)-B—one had a flowering time of 56 days and very nearly qualifies as having a spring flowering habit. This suggests that even after 3 backcrosses to winter B. napus, the progeny of the winter B. napus×rapid-cycle B. rapa cross disclosed herein can yield B. napus with a spring flowering habit.

Although not shown in Table 4, the earliest-flowering plant of the Wichita backcross, F1(BC2)-F, population was also crossed with Westar and another spring B. napus line. The resultant F1 hybrid had improved vigor and appeared to have better yield, based on leaf size, larger pod size, and more seeds, when compared to either parent line.

Example 5

Comparison to Spring×Winter B. napus Crosses

A first spring×winter B. napus population was created by crossing a spring B. napus line with Columbus; as in Example 1, Columbus was male sterile and served as the female parent. The process used in Example 1 to produce F1-C, i.e., crossing the FPS rapid-cycle B. rapa and Columbus, was repeated. Five plants of each cross were produced and the resultant seed was grown at SGCs for at least 100 days. The plant with the earliest flowering time for the spring×Columbus cross (designated here as SW-F1) flowered in 43 days. The plant with the earliest flowering time for the FPS×Columbus cross (designated here as FPSC-F1) flowered in 31 days.

SW-F1 and FPSC-F1 were each backcrossed with Columbus. Thirty plants of each cross were produced and the resultant seed was grown at SGCs for at least 100 days. The time to the earliest flowering was noted for those plants that did flower; if no flowers were seen in that time, the plant was noted as non-flowering. The results, including for each cross the shortest first flowering time for any of the 30 plants and the average first flowering time for those plants that did flower, are set forth in Table 5.

TABLE 5

| Female Parent | Male Parent | Total Plants | Flowering Plants (%) | Shortest Days of Earliest Flowering (Under SGCs) | Average Days of Earliest Flowering | No. of Spring Plants |
|---|---|---|---|---|---|---|
| Columbus | SW-F1 | 30 | 3 (10%) | 83 | 89 | 0 |
| Columbus | FPSC-F1 | 30 | 18 (60%) | 35 | 59 | 9 |

These results again highlight the surprising utility achieved by crossing rapid-cycle B. rapa with winter B. napus in accordance with aspects of the invention. The SWC-F1 parent in the backcross of Table 5 had a spring flowering habit that was reinforced through multiple generations of spring backcrosses and selection for spring flowering habit. All thirty of the backcrosses of that plant with a winter line had a winter flowering habit, i.e., the spring conversion efficiency of the cross was 0%, and the average number of days to earliest flowering of the three lines that did flower in the time allotted was almost 90 days. In contrast, the FPSC-F1 backcross yielded 18 plants that flowered in the same time, with one reaching first flower in just 35 days. Of those 18 plants, 9 had a spring flowering habit, representing a 30% spring conversion efficiency (9 of the 30 total plants), with an average among those 9 plants of 47 days to earliest flowering.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. When the claims use the word "or" in reference to a list of two or more items, that word covers all of the following interpretations of the word: any of the items in the list, all of the items in the list, and any combination of the items in the list.

The above detailed descriptions of embodiments of the invention are not intended to be exhaustive or to limit the invention to the precise form disclosed above. Although specific embodiments of, and examples for, the invention are described above for illustrative purposes, various equivalent modifications are possible within the scope of the invention, as those skilled in the relevant art will recognize. For example, while steps are presented in a given order, alternative embodiments may perform steps in a different order. The various embodiments described herein can also be combined to provide further embodiments.

Unless otherwise indicated, all numbers expressing quantities of ingredients, properties such as molecular weight, percentages, reaction conditions, and so forth used in the specification and claims are to be understood as being modified by the term "about." Accordingly, unless indicated to the contrary, the numerical parameters set forth are approximations that may depend upon the desired properties sought.

In general, the terms used in the following claims should not be construed to limit the invention to the specific embodiments disclosed in the specification, unless the above detailed description explicitly defines such terms. Unless otherwise indicated, all numbers expressing quantities of ingredients, properties such as molecular weight, percentages, reaction conditions, and so forth used in the specification and claims are to be understood as being modified by the term "about." Accordingly, unless indicated to the contrary, the numerical parameters set forth are approximations that may depend upon the desired properties sought.

We claim:

1. A method for producing a modified Brassica napus, comprising:
   crossing a first winter B. napus line with a rapid-cycle B. rapa line having a mean flowering time under standardized growing conditions of no greater than 20 days in a first cross, thereby producing an F1 modified B. napus plant that has a spring flowering habit; and
   thereafter, crossing seed from the F1 modified B. napus plant with a second winter B. napus line in a second cross to produce a plant that has a spring flowering habit.

2. The method of claim 1 wherein the first and second winter B. napus lines are the same line.

3. The method of claim 1 wherein the first and second winter B. napus lines are different lines.

4. The method of claim 1 wherein the first cross has a spring conversion efficiency of at least about 80%.

5. The method of claim 1 wherein the plant produced in the second cross is referred to as a BC1 plant, the method further comprising crossing the BC1 plant with a third winter B. napus line in a third cross to produce a plant population and selecting from the population a second plant that has a spring flowering habit.

6. The method of claim 1 wherein the plant produced in the second cross is referred to as a BC1 plant, the method further comprising crossing the BC1 plant with a third winter B. napus line in a third cross to produce a plant population and selecting from the population a second plant that has a winter flowering habit.

7. The method of claim 5, wherein the third winter B. napus line is different from at least one of the first and second winter B. napus lines.

8. The method of claim 1 wherein the plant produced in the second cross is referred to as a BC1 plant, the method further comprising crossing the BC1 plant with a spring B. napus line to produce a hybrid plant that has a spring flowering habit.

9. The method of claim 1 wherein the plant produced in the second cross is referred to as a BC1 plant, the method further comprising crossing the BC1 plant with a third winter B. napus line to produce a restored winter plant that has a winter flowering habit.

10. The method of claim 9 wherein the third winter line is the same line as at least one of the first and second winter lines.

11. The method of claim 9 wherein the third winter line is a different line from both of the first and second winter lines.

12. The method of claim 9 further comprising crossing the restored winter plant with a fourth winter B. napus line.

13. A B. napus plant having a spring flowering habit, said plant being produced by the method of claim 1.

14. Seed of the plant of claim 13 or progeny of said seed, said seed or progeny having a winter allele for at least one of vfn1, vfn2, and vfn3 loci but yielding a plant having a spring flowering habit.

15. A method for producing a modified Brassica napus having a winter flowering habit, comprising:

crossing a first winter *B. napus* line with a rapid-cycle *B. raga* line having a mean flowering time under standardized growing conditions of no greater than 20 days in a first cross, thereby producing an F1 modified *B. napus* plant that has a spring flowering habit;

thereafter, crossing the F1 modified *B. napus* plant with a second winter *B. napus* line in a second cross to produce a first backcross population and selecting from the first backcross population a first backcross (BC1) plant that has a spring flowering habit; and thereafter, crossing the BC1 plant with a third winter *B. napus* line in a third cross to produce a second backcross plant population and selecting from the second backcross population at least one second backcross (BC2-W) plant that has a winter flowering habit.

16. The method of claim 15 wherein the third winter line is the same line as at least one of the first and second winter lines.

17. The method of claim 15 further comprising crossing the BC1 plant with a third winter *B. napus* line in a fourth cross to produce a BC1 backcross progeny population and selecting from the BC1 backcross progeny population at least one BC1 progeny backcross plant that has a spring flowering habit.

18. A *B. napus* plant having a winter flowering habit, said plant being produced by the method of claim 15.

19. Seed of the plant of claim 18.

* * * * *